US00PP29276P3

(12) United States Plant Patent
Bergman

(10) Patent No.: US PP29,276 P3
(45) Date of Patent: May 8, 2018

(54) ***MANDEVILLA* PLANT NAMED 'MANZ0001'**

(50) Latin Name: ***Mandevilla sanderi* (Hemsl.) Woodson**
Varietal Denomination: MANZ0001

(71) Applicant: SYNGENTA PARTICIPATIONS AG, Basel (CH)

(72) Inventor: Wendy R. Bergman, Gilroy, CA (US)

(73) Assignee: Syngenta Participations AG, Basel (CH)

( * ) Notice: Subject to any disclaimer, the term of this patent is extended or adjusted under 35 U.S.C. 154(b) by 30 days.

(21) Appl. No.: 14/999,791

(22) Filed: Jun. 27, 2016

(65) Prior Publication Data

US 2017/0374776 P1 Dec. 28, 2017

(51) Int. Cl.
*A01H 5/02* (2018.01)

(52) U.S. Cl.
USPC ..... Plt./232
CPC ..... *A01H 5/02* (2013.01)

(58) Field of Classification Search
USPC ..... Plt./232
See application file for complete search history.

(56) References Cited

PUBLICATIONS

UPOV hit on *Mandevilla* plant named 'Manz0001', CA PBR 15-8597, filed Apr. 10, 2015.*

* cited by examiner

*Primary Examiner* — Anne Marie Grunberg
(74) *Attorney, Agent, or Firm* — Dale Skalla

(57) ABSTRACT

A new *Mandevilla* plant named 'MANZ0001' particularly distinguished by its large dark pink flowers, glossy and smooth medium green foliage, bushy plant habit with a tendency to produce vines under low light growing conditions and with excellent branching and floriferousness.

1 Drawing Sheet

Latin name of the genus and species of the plant claimed: *Mandevilla sanderi* (Hemsl.) Woodson.

Varietal denomination: 'MANZ0001'.

BACKGROUND OF THE NEW PLANT

The present invention comprises a new *Mandevilla*, botanically known as *Mandevilla sanderi*, and hereinafter referred to by the variety name 'MANZ0001'.

'MANZ0001' is a product of a planned breeding program. The new cultivar has large dark pink flowers, glossy and smooth medium green foliage, bushy plant habit with a tendency to produce vines under low light growing conditions and with excellent branching and floriferousness.

'MANZ0001' originates from a hybridization made in a controlled breeding program in Hillscheid, Germany. The pollinations were made in 2007.

The female parent was an unpatented, proprietary plant identified as 'K05-2008-2' and having red flower color and large flower size.

The male parent of 'MANZ0001' was an unpatented, proprietary plant identified as 'K04-1263-77' with red flower color and a vining habit.

The resulting seeds were sown in August 2009 and 'MANZ0001' was selected as one flowering plant within the progeny of the stated cross in July 2010 in a greenhouse in Gilroy, Calif.

The first act of asexual reproduction of 'MANZ0001' was accomplished when vegetative cuttings were propagated from the initial selection in August 2010 in a controlled environment in Gilroy, Calif.

BRIEF SUMMARY OF INVENTION

Horticultural examination of plants grown from cuttings of the plant initiated in May 2011 in Gilroy, Calif., and continuing thereafter, has demonstrated that the combination of characteristics as herein disclosed for 'MANZ0001' are firmly fixed and are retained through successive generations of asexual reproduction.

'MANZ0001' has not been observed under all possible environmental conditions. The phenotype may vary significantly with variations in environment such as temperature, light intensity and day length.

A Plant Breeder's Right for this cultivar was applied for in Canada on Apr. 10, 2015, No. 15-8597. 'MANZ0001' has not been made publicly available prior to the effective filing date of this application, notwithstanding any disclosure that may have been made less than one year prior to the effective filing date of this application by the inventor or another who obtained 'MANZ0001' directly from the inventor.

The following traits have been repeatedly observed and are determined to be basic characteristics of the new variety. The combination of these characteristics distinguishes this *Mandevilla* as a new and distinct variety.

BRIEF DESCRIPTION OF THE PHOTOGRAPHS

Figure 1:
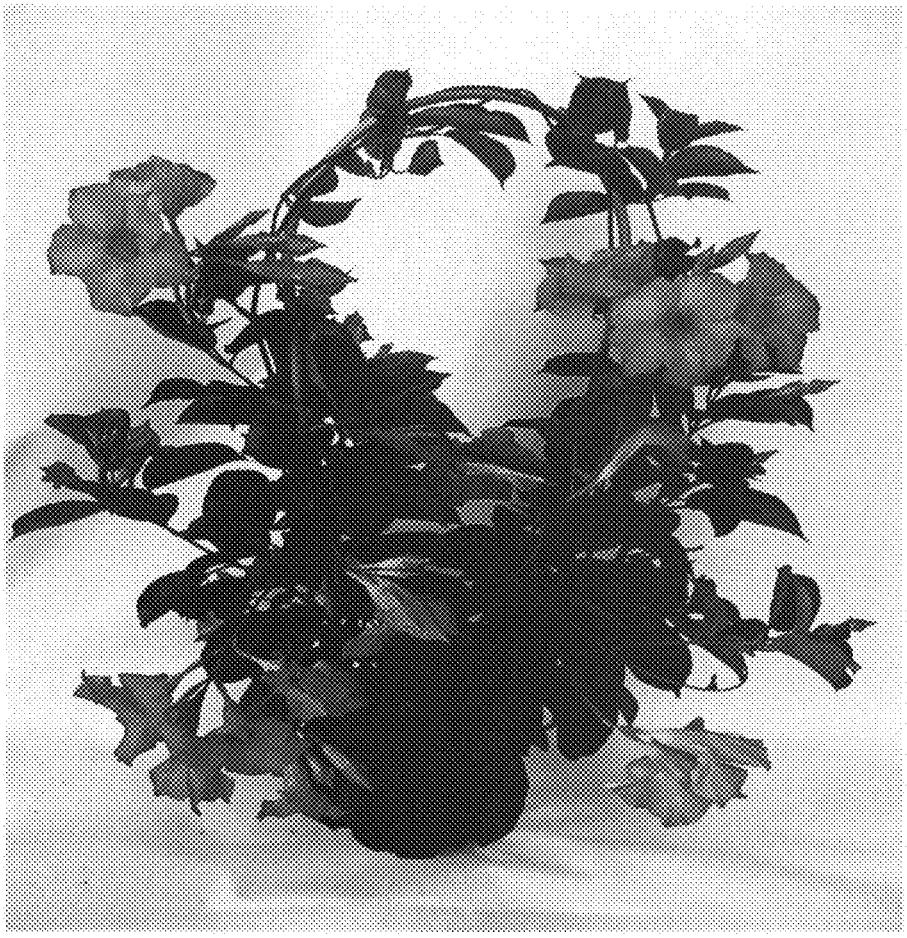
Figure 2:
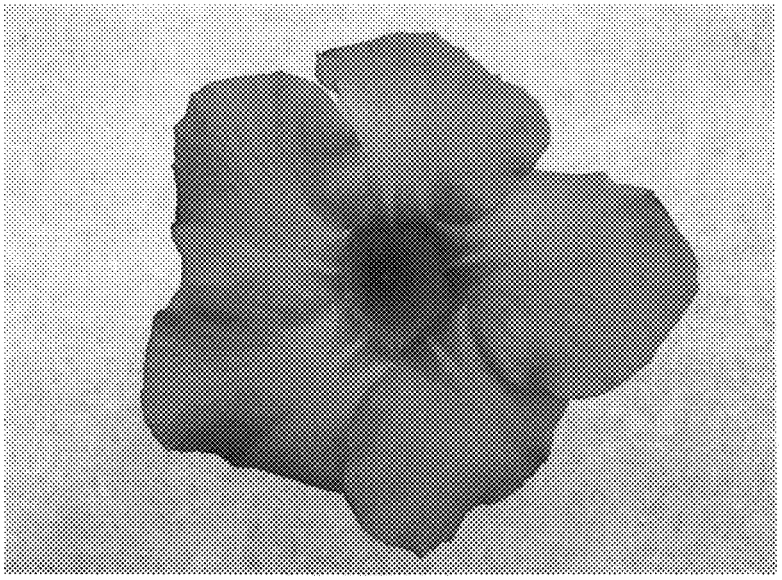

The accompanying photographic drawings show typical flower and foliage characteristics of 'MANZ0001' with colors being as true as possible with an illustration of this type. The photographic drawings show in FIG. 1, a flowering potted plant of the new variety and in FIG. 2, a close-up of the flowers.

DETAILED BOTANICAL DESCRIPTION

The aforementioned photographs were taken Jun. 8, 2016 in Gilroy, Calif. The plants were growing in 11 cm pots on benches in a greenhouse. They were about 5 months in age.

TABLE 1

DIFFERENCES BETWEEN THE NEW VARIETY 'MANZ0001' AND A SIMILAR VARIETY

| Traits | 'MANZ0001' | 'FISRIX HOPINK' (Rio Hot Pink U.S. Plant Pat. No. 20,672) |
|---|---|---|
| Overall flower color: | Lighter color | Darker color |
| Flower size: | Larger | Smaller |
| Foliage: | Larger | Smaller |
| Plant size or habit: | Larger, more vigorous | Smaller, less vigorous |
| Flowering response: | Faster, by several weeks | Slower, by several weeks |

Plant:

*Form, growth and habit*.—Perennial or sub-shrub, herbaceous younger stems, woody at base of older stems, spreading, semi-upright, with moderate tendency of developing vines depending on season and light intensity. Time for producing a commercial, flowering plant approximately is 12 weeks for one plant in a quart size container.

*Plant height*.—40 cm.

*Plant height* (*inflorescence included*).—45 cm.

*Plant width*.—25 cm.

Roots:

*Number of days to initiate roots*.—About 16-20 days at about 22 degrees C.

*Number of days to produce a rooted cutting plant*.—5 weeks at about 22 degrees C.

*Type*.—Fibrous, a little fleshy, free branching.

*Color*.—RHS N155D.

Foliage:

*Arrangement of leaves*.—Simple leaf, opposite and decussate.

*Immature leaf, color upper surface*.—RHS 137B.

*Immature leaf, color lower surface*.—RHS 146B with some anthocyanin overlay.

*Mature leaf, color upper surface*.—RHS 139A.

*Mature leaf, color lower surface*.—RHS 137B.

*Length*.—9.5-11.0 cm.

*Width*.—6.0-7.5 cm.

*Shape*.—Ovate.

*Base shape*.—Rounded.

*Apex shape*.—Cuspidate.

*Margin*.—Entire.

*Texture, upper surface*.—Smooth, glossy, glabrous.

*Texture, lower surface*.—Smooth, glossy, glabrous.

*Pattern of leaf veins*.—Pinnate.

*Color of veins, upper surface*.—RHS 138B.

*Color of vein* (*midrib*), *lower surface*.—RHS 147D.

*Petiole color*.—RHS 138A.

*Length*.—1.7 cm.

*Diameter*.—0.25 cm.

*Petiole, texture*.—Glabrous.

Stem:

*Branching characteristics*.—Moderately free branching.

*Quantity of main branches per plant*.—3-5.

*Color of stem*.—RHS 138A, no anthocyanin.

*Length of stem*.—30-37 cm.

*Diameter* (*at about mid point*).—0.4 cm.

*Length of internodes*.—3-7 cm.

*Stem, texture*.—Smooth and glabrous.

Inflorescence:

*Type of inflorescence*.—Raceme of several flowers, emerging from nodes of the stem.

*Number of flowers per inflorescence*.—5-9.

*Blooming habit*.—Continuously through the summer months.

*Quantity of flowers per plant*.—About 15 in various stages of development.

*Lastingness of individual blooms on the plant*.—Approximately 8-10 days, depending on temperature.

*Fragrance*.—Absent.

Peduncle:

*Color*.—Green, RHS 141B.

*Length*.—5.0-7.0 cm.

*Diameter*.—0.3-0.4 cm.

*Texture*.—Smooth, glabrous, somewhat glossy.

Bud (just before opening/showing color):

*Color*.—RHS 58C at the tip, the middle part is alternating RHS 58C and RHS 142D, the base is RHS 142C.

*Length*.—8.0-8.5 cm.

*Width*.—1.7-2 cm.

*Shape*.—Elongated, spindle shape.

Immature flower:

*Diameter*.—7 cm.

*Vertical diameter*.—About 4.5 cm.

*Color upper surface*.—RHS 58B with tones of RHS 54B.

*Color lower surface*.—RHS 54A with lighter tones.

Mature flower:

*Shape*.—Funnelform, funnel shaped base, formed by 5 partly fused petals, with the petal lobes opening outwards, and a little overlapping.

*Flower, horizontal diameter*.—9.0 cm.

*Flower, vertical diameter*.—About 6.5 cm.

*Flower, diameter of the funnel*.—2 cm.

*Flower color, general*.—Dark pink, and with no strong fading.

*Flower color, upper surface*.—RHS 57B with shades of RHS 54B and RHS 55B. Two elongated triangular marks arising from the corolla opening on each petal RHS 53B.

*Flower color, lower surface*.—RHS 54A with lighter tones.

*Color of the funnel, inner side*.—RHS 26B.

*Color of the funnel, outside*.—RHS 58D and narrow vertical stripes of RHS 1C.

*Petal, shape*.—Roughly ovate, asymmetric.

*Petal apex shape*.—Acute.

*Petal base shape*.—Fused.

*Petal margin*.—Mainly entire.

*Petal length, from the corolla opening*.—3.8 cm.

*Petal width, maximum*.—4.8 cm.

*Corolla, texture of upper surface*.—Glabrous, papillose.

*Corolla, texture of lower surface*.—Glabrous, papillose.

*Pedicel, color*.—Light green, RHS 145B.

*Length*.—1.3 cm.

*Diameter*.—0.25 cm.

*Pedicel, texture*.—Smooth, glabrous.

Calyx:

*Form*.—5 sepals, closely attached to the base of the flower.

*Color, visible outer surface*.—RHS 145C.

*Length*.—1.3 cm.

*Width.*—0.5 cm.
*Shape*.—Subulate.
*Apex shape*.—Acute.
*Base*.—Fused.
*Margins*.—Entire.
*Texture, upper surface*.—Glabrous.

Reproductive organs:

Gynoecium:

*Pistil.*—1, with a 5-lobed stigma.
*Style length.*—2.0 cm.
*Diameter.*—0.05 cm.
*Style color.*—RHS 150C.
*Stigma color*.—RHS 145B.
*Stigma shape*.—Five lobed.
*Ovary color*.—RHS 145B.

Androecium:

*Stamens.*—5, connivent, surrounding the style and stigma.
*Filaments*.—Fused with the base of the flower.
*Anther*.—Elongated.
*Anther color*.—RHS 18B.
*Anther length.*—1.0 cm.
*Color of pollen*.—RHS 4D.
*Pollen amount*.—Moderate.

Fertility/seed set: Has not been observed on this hybrid.

Disease/pest resistance: Has not been observed on this hybrid.

What is claimed is:

1. A new and distinct variety of *Mandevilla* plant named 'MANZ0001' substantially as illustrated and described herein.

* * * * *